US006992201B2

(12) United States Patent
Scholz et al.

(10) Patent No.: US 6,992,201 B2
(45) Date of Patent: Jan. 31, 2006

(54) PROCESS FOR PREPARING PHOSPHITES AND TRANSITION METAL COMPLEXES

(75) Inventors: Ulrich Scholz, Mülheim (DE); Erasmus Vogl, Leverkusen (DE); Arne Gerlach, Odenthal (DE); Jorma Hassfeld, Nienburg (DE)

(73) Assignee: Bayer Aktiengesellschaft, Leverkusen (DE)

( * ) Notice: Subject to any disclaimer, the term of this patent is extended or adjusted under 35 U.S.C. 154(b) by 30 days.

(21) Appl. No.: 10/650,012

(22) Filed: Aug. 26, 2003

(65) Prior Publication Data

US 2004/0116726 A1    Jun. 17, 2004

(30) Foreign Application Priority Data

Aug. 30, 2002 (DE) ............................... 102 408 03

(51) Int. Cl.
*C07F 15/00* (2006.01)
*C07F 9/02* (2006.01)
*B01J 31/00* (2006.01)

(52) U.S. Cl. .................. 556/20; 556/136; 568/12; 568/14; 502/162

(58) Field of Classification Search ............. 556/20, 556/136; 568/12, 14; 502/162

See application file for complete search history.

(56) References Cited

U.S. PATENT DOCUMENTS

| 5,616,767 | A | 4/1997 | Enlow et al. ............. 558/92 |
| 5,998,326 | A | 12/1999 | Hafner et al. ............ 502/155 |
| 6,204,347 | B1 | 3/2001 | Hafner et al. ............ 523/172 |
| 2003/0171608 | A1 | 9/2003 | Reetz et al. ............. 558/348 |

FOREIGN PATENT DOCUMENTS

WO    01/94278    12/2001

OTHER PUBLICATIONS

Manfred T. Reetz* and Gerlinde Mehler; Angew. Chem. Int. Ed. (month unavailable) 2000, 39, No. 21, pp. 3889-3890; "Highly Enantioselective Rh-Catalyzed Hydrogenation Reactions Based on Chiral Monophosphite Ligands".

Patrick H. Dussault* and Kevin R. Woller; J. Org. Chem. (month unvailable) 1997, 62, pp. 1556-1559; "Approaches to Stereoselective Dioxygenation of Alkenes: Chiral Phosphite Ozonides" American Chemcal Society; Journal of Organic Chemistry, v62, p. 1556, Dussault Supple-mental pp. 1-14.

Jean-Michel Brunel and Gerard Buono*; J. Org. Chem. (month unavailable) 1993, 58, pp. 7313-7314; "A New and Efficient Method for the Resolution of 1,1'-Binaphthalene-2,2-diol".

Cai, Jue Xiao et al: "A new convenient method for the resolution of 1,1'-binaphthalene- 2,2' -diol via a phosphite using (-) -menthol as resolving agent" Chinese Chemical Letters (2002), 13(7), 617-619, 2002, XP001172891 *Seite 618, Unten *.

Bedekar, A.V. et al: "Intramolecular asymmetric olefination of binaphythyl phosphonate derivatives of 1,3-diketones" Tetrahedron: Asymmetry, Elsevier Schience Publishers, Amsterdam, NL, Bd. 13, Nr. 7, May 2, 2002, Seiten 721-727, XP004354864 ISSN: 0957-4166 *das ganze Dokument*.

Chen W et al: "Enantioselective hydrogenation with inexpensive, easily available monodentate phosphite ligands" Tetrahedron Letters, Elsevier Science Publishers, Amsterdam, NL, Bd. 42, Nr. 15, Apr. 9, 2001, Seiten 2897-2899, XP004232343 ISSN: 0040-4039 *das ganze Dokument*.

Chen W et al: "Asymmetric activation of conformationally flexible monodentate phosphites for enantioselective hydrogenation" Tetrahedron Letters, Elsevier Science Publishers, Amsterdam, NL, Bd. 42, Nr. 49, Dec. 3, 2001, Seiten 8737-8740, XP004321537 ISSN: 0040-4039 *daz ganze Dokument*.

*Primary Examiner*—Porfirio Nazario-Gonzalez
(74) *Attorney, Agent, or Firm*—Diderico van Eyl

(57) ABSTRACT

The present invention relates to a process for preparing phosphites and their transition metal complexes and also to their use in catalytic processes.

16 Claims, No Drawings

PROCESS FOR PREPARING PHOSPHITES AND TRANSITION METAL COMPLEXES

BACKGROUND OF THE INVENTION

1. Field of the Invention

The present invention relates to a process for preparing phosphites and their transition metal complexes and also to their use in catalytic processes.

2. Brief Description of the Prior Art

Phosphites have achieved great importance, especially in homogeneous catalysis, since they are capable of complexing to a transition metal, controlling its catalytic activity and in some cases transferring stereochemical information to a substrate.

It is known that stereoisomerically enriched phosphites which are derived from 2,2'-binapthols in particular are suitable for asymmetric hydrogenations (see also DE 100 27 505 A1 and Reetz, Mehler, Angew Chem., Int. Ed. Engl. 2000, 39, 21, 3889). The stereoisomerically enriched phosphites are prepared by initially reacting the corresponding stereoisomerically enriched 2,2'-binaphthols with phosphorus trichloride to give binaphthylphosphorus chlorides and subsequently reacting these with monoalcohols.

Alternatively, the conversion can be effected at −78° C. using a monoalkoxide (see also P. H. Dussault, K. R. Woller, J. Org. Chem. 1997, 62, 1556–1559).

A disadvantage of this process is that in the preparation of binaphthylphosphorus chlorides, one has to use very low temperatures of −78° C., which can only be realized on the industrial scale at great cost and inconvenience.

Illustratively, EP-A 729 965 discloses a process for preparing biphenyl phosphites in which phosphorus trichloride is additionally reacted with a monoalcohol and subsequently with a biphenol in a one-pot reaction. A disadvantage of this reaction is that, in the second step, an amine is required as a base, which forms a hydrochloride soluble in the reaction medium. Also, the operation has to be effected in high concentration and in aromatic hydrocarbons as solvents, in order to achieve high yields. However, such specific conditions are unacceptable for industrial use, because broad application to differently substituted phosphites is hardly possible.

J. M. Brunel, G. Buono, J. Org. Chem. 1993, 58, 7313–7314 disclose a process for optical resolution of 1,1'-binaphthyl-2,2'-diol which proceeds via the preparation of diastereomeric binaphthylmenthyl phosphites by initially reacting phosphorus trichloride with one equivalent of L-menthol and subsequently adding the racemic 1,1'-binaphthyl-2,2'-diol. A disadvantage of this process is that the intermediate is not isolated and is therefore not purified.

There was therefore a need to provide a process for preparing phosphites and in particular stereoisomerically enriched phosphites which ensures high yields and high product purities.

SUMMARY OF THE INVENTION

A process has now been found for preparing compounds of the formula (I)

where
D is an unsubstituted or substituted 1,1'-biphenyl-2,2'-diyl- or 1,1'-binaphthyl-2,2'-diyl radical and
$R^1$ is a radical selected from the group of $C_1$–$C_{12}$-alkyl, $C_2$–$C_{12}$-alkenyl, $C_1$–$C_{12}$-haloalkyl, $C_5$–$C_{15}$-arylalkyl and $C_4$–$C_{14}$-aryl, with the proviso that
$R^1$ has a molar mass of 215 or less,
characterized by the following process steps:
in a step a)
compounds of the formula (II)

$$PHal_3 \qquad (II)$$

where Hal is in each case independently, but preferably identically, chlorine, bromine or iodine, preferably chlorine,
optionally in the presence of a base
are initially reacted with compounds of the formula (III)

$$R^1\text{—OH} \qquad (III)$$

where
$R^1$ is as defined above
to give compounds of the formula (IV)

$$R^1OPHal_2 \qquad (IV)$$

where
$R^1$ and Hal are each as defined above,
in a step b)
the compounds of the formula (IV), resulting from step a) are distillatively purified and
in a step c),
the compounds of the formula (IV) purified in step b) are reacted, optionally and preferably in the presence of a base,
with compounds of the formula (V)

$$D(OH)_2 \qquad (V)$$

where
D is as defined above
to give compounds of the formula (I).

DETAILED DESCRIPTION OF THE INVENTION

For the purpose of the invention, all radical definitions, parameters and illustrations listed hereinabove and hereinbelow, in general or within areas of preference, i.e. the particular areas and areas of preference, may be combined as desired.

Alkyl, alkylene, alkenyl and alkoxy are in each case independently a straight-chain, cyclic, branched or unbranched alkyl, alkylene, alkenyl or alkoxy radical respectively, and the radicals mentioned may optionally be further substituted by $C_1$–$C_4$-alkoxy radicals. The same applies to the nonaromatic moiety of an arylalkyl radical.

$C_1$–$C_4$-Alkyl is, for example, methyl, ethyl, n-propyl, isopropyl, n-butyl, sec-butyl and tert-butyl. $C_1$–$C_8$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, 1-ethyl-2-methylpropyl, n-heptyl and n-octyl, $C_1$–$C_{12}$-alkyl is further additionally, for example, adamantyl, the isomeric menthyls, n-nonyl, n-decyl and n-dodecyl.

$C_1$–$C_4$-Alkoxy is, for example, methoxy, ethoxy, n-propoxy, isopropoxy, n-butoxy, sec-butoxy and tert-butoxy. $C_1$–$C_8$-alkoxy is additionally n-pentoxy, 1-methylbutoxy, 2-methylbutoxy, 3-methylbutoxy, neopentoxy, 1-ethylpropoxy, cyclohexoxy, cyclo-pentoxy, n-hexoxy, n-octoxy, and $C_1$–$C_{12}$-alkoxy is still further additionally adamantoxy, the isomeric menthoxy radicals, n-decoxy and n-dodecoxy.

$C_2$–$C_{12}$-Alkenyl is, for example, vinyl, 1-propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 1-heptenyl, 1-octenyl or 2-octenyl.

Halogenalkyl is in each case independently a straight-chain, cyclic, branched, or un-branched alkyl radical which is singularly, multiply, or fully substituted by chlorine or fluorine atoms.

For example, $C_1$–$C_{12}$-fluoroalkyl is trifluoromethyl, 2,2,2-trifluoroethyl, 2,2,2-tri-chloroethyl and pentafluoroethyl.

Aryl is in each case independently a heteroaromatic radical having 4 to 14 framework carbon atoms of which no, one, two or three framework carbon atoms per cycle, but at least one framework carbon atom in the entire molecule, may be substituted by heteroatoms selected from the group of nitrogen, sulphur or oxygen, but is preferably a carbocyclic aromatic radical having 6 to 14 framework carbon atoms.

Examples of carbocyclic aromatic radicals having 6 to 14 framework carbon atoms are phenyl, naphthyl or fluorenyl, heteroaromatic radicals having 4 to 14 framework carbon atoms of which no, one, two or three framework carbon atoms per cycle, but at least one framework carbon atom in the entire molecule may be substituted by heteroatoms selected from the group of nitrogen, sulphur or oxygen, are furanyl, pyridinyl, oxazolyl, benzofuranyl, dibenzofuranyl or quinolinyl.

The carbocyclic aromatic radical or heteroaromatic radical may also be substituted by up to five identical different substituents per cycle which are selected from the group of chlorine, fluorine, bromine, cyano, $C_1$–$C_{12}$-alkyl, $C_1$–$C_{12}$-haloalkyl, $C_1$–$C_{12}$-alkoxy, di($C_1$–$C_8$-alkyl)amino, COO($C_1$–$C_8$-alkyl), CON($C_1$–$C_8$-alkyl)$_2$, COO($C_5$–$C_{15}$-arylalkyl), COO($C_4$–$C_{14}$-aryl), CO($C_1$–$C_8$-alkyl), $C_5$–$C_{15}$-arylalkyl or tri($C_1$–$C_8$-alkyl)siloxyl.

Arylalkyl in each case independently has a straight-chain, cyclic, branched or un-branched alkyl radical which may be singularly, multiply or fully substituted by aryl radicals as defined above.

$C_5$–$C_{15}$-Arylalkyl is, for example, benzyl, (R)— and (S)-1-phenylethyl, 1-phenylpropyl, 2-phenylpropyl, 1-phenyl-1-methylethyl, 1-, 2-, 3- or 4-phenylbutyl, 1-naphthylmethyl, 1-naphthylethyl and naphthyl-1-methylethyl.

For the purposes of the invention, protected formyl is a formyl radical which is protected by conversion to an aminal, acetal or mixed aminalacetal, and aminals, acetals and mixed aminalacetals may be acyclic or cyclic.

For the purposes of the invention, protected hydroxy is a hydroxy radical which is protected by conversion to an acetal, carbonate, carbamate or carboxylate. Examples thereof include conversion to a tetrahydropyranyl adduct, or to a benzyloxycarbonyl, allyloxycarbonyl or tert-butyloxycarbonyl derivative.

The preferred substitution patterns for the compounds of the formulae (I) and (III) and (V) are defined hereinbelow:

$R^1$ is preferably a radical which is selected from the group of $C_1$–$C_8$-alkyl, $C_5$–$C_{15}$-arylalkyl and $C_4$–$C_{14}$-aryl, with the proviso that $R^1$ has a molar mass of 200 or less.

$R^1$ is particularly preferably a radical selected from the group of $C_1$–$C_8$-alkyl, benzyl and phenyl, benzyl and phenyl being optionally mono-, di- or tri- substituted by radicals which are each independently selected from the group of chlorine, fluorine, methyl, ethyl, isopropyl, tert-butyl, methoxy, ethoxy, iso-propoxy, dimethylamino, diethylamino, acetyl, trifluoromethyl and cyano, with the proviso that $R^1$ has a molar mass of 200 or less.

$R^1$ is very particularly preferably isopropyl, neopentyl, benzyl and phenyl.

Preference is given to using stereoisomerically enriched, in particular enantiomerically enriched, compounds of the formula (V) for the process according to the invention. For the purpose of the invention, enantiomerically enriched includes enantiomerically pure compounds or any desired mixtures of enantiomers in which one enantiomer is present in an enantiomeric excess, also referred to hereinbelow as ee (enantiomeric excess), in comparison to the other enantiomer. This enantiomer excess in the case of compounds of the formula (V) is preferably 10 to 100% ee, particularly preferably 90% to 100% ee and very particularly preferably 98 to 100% ee.

In formulae (I) and (V),

D is preferably an unsubstituted or substituted 1,1'-biphenyl-2,2'-diyl radical of the formula (VI)

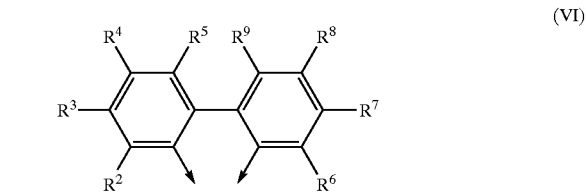

(VI)

or is an unsubstituted or substituted 1,1'-binaphthyl-2,2'-diyl radical of the formula (VII)

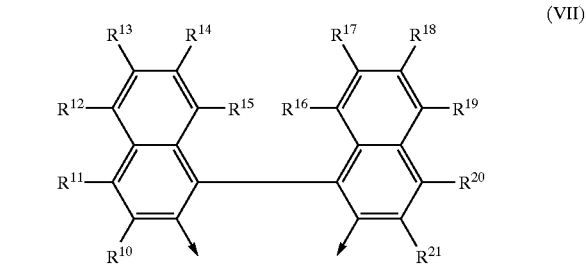

(VII)

where the radicals $R^2$ to $R^{20}$ are in each case independently selected from the group of hydrogen, fluorine, chlorine, bromine, cyano, protected hydroxyl, $C_1$–$C_{12}$-alkyl, $C_1$–$C_{12}$-halogenalkyl, $C_1$–$C_{12}$-alkoxy, $C_1$–$C_8$-alkylthio, free or protected formyl, $C_4$–$C_{14}$-aryl, tri($C_1$–$C_8$-alkyl)siloxyl or radicals of the formula (VIII)

$$A\text{-}B\text{-}E\text{-}F \tag{VIII}$$

where, each independently,
A is absent or is a $C_1$–$C_8$-alkylene radical and
B is absent or is oxygen, sulphur or $NR^{21}$
  where
  $R^{21}$ is hydrogen, $C_1$–$C_{12}$-alkyl or $C_4$–$C_{14}$-aryl and
  E is a carbonyl group and
  F is $R^{22}$, $OR^{22}$, $NHR^{23}$ or $NR^{23}R^{24}$
    where
    $R^{22}$ is $C_1$–$C_{12}$-alkyl or $C_6$–$C_{10}$-aryl and
    $R^{23}$ and $R^{24}$ are each independently $C_1$–$C_8$-alkyl or $C_4$–$C_{14}$-aryl, or $NR^{23}R^{24}$ together is a cyclic amino radical having 4 to 12 carbon atoms.

Radicals from $R^2$ to $R^{20}$ which are in each case adjacent may also together form a nonaromatic ring. Two of the radicals from $R^2$ to $R^{20}$ may also be bridging. The useful bridges are, for example and with preference, of the formula (IX)

$$\text{—O-G}^1\text{-K-G}^2\text{-O—} \tag{IX}$$

where, in each case independently,
$G^1$ and $G^2$ may either be omitted, be a carbonyl group or be a carbonylamino group and
K may be unsubstituted or substituted $C_2$–$C_6$ alkylene.
D is particularly preferably an unsubstituted or substituted 1,1'-biphenyl-2,2'-diyl radical of the formula (VI) or an unsubstituted or substituted 1,1'-biphenyl-2,2'-diyl radical of the formula (VII) where the radicals $R^2$ to $R^{20}$ are in each case independently selected from the group of hydrogen, fluorine, chlorine, $C_1$–$C_8$-alkyl, $C_1$–$C_8$-halogenalkyl or $C_1$–$C_8$-alkoxy.

The process according to the invention is suitable in particular for preparing the following compounds:
((S)-5,5'-dichloro-6,6'-dimethoxy-1,1'-biphenyl-2,2'-diyl) isopropyl phosphite
((R)-5,5'-dichloro-6,6'-dimethoxy-1,1'-biphenyl-2,2'-diyl) isopropyl phosphite
((R)-5,5'-dichloro-6,6'-dimethoxy-1,1'-biphenyl-2,2'-diyl)-(R)-1-phenylethyl phosphite
((R)-5,5'-dichloro-6,6'-dimethoxy-1,1'-biphenyl-2,2'-diyl)-(S)-1-phenylethyl phosphite
((S)-5,5'-dichloro-6,6'-dimethoxy-1,1'-biphenyl-2,2'-diyl)-(R)-1-phenylethyl phosphite
((S)-5,5'-dichloro-6,6'-dimethoxy-1,1'-biphenyl-2,2'-diyl)-(S)-1-phenylethyl phosphite
((S)-5,5'-dichloro-6,6'-dimethoxy-1,1'-biphenyl-2,2'-diyl) cyclohexyl phosphite
((R)-5,5'-dichloro-6,6'-dimethoxy-1,1'-biphenyl-2,2'-diyl) cyclohexyl phosphite
((S)-5,5'-dichloro-6,6'-dimethoxy-1,1'-biphenyl-2,2'-diyl) phenyl phosphite
((R)-5,5'-dichloro-6,6'-dimethoxy-1,1'-biphenyl-2,2'-diyl) phenyl phosphite
((S)-5,5'-dichloro-6,6'-dimethoxy-1,1'-biphenyl-2,2'-diyl)-2,6-dimethylphenyl phosphite
((R)-5,5'-dichloro-6,6'-dimethoxy-1,1'-biphenyl-2,2'-diyl)-2,6-dimethylphenyl phosphite
((S)-5,5',6,6'-tetramethyl-3,3'-bis(tert-butyl)-1,1'-biphenyl-2,2'-diyl)isopropyl phosphite
((R)-5,5',6,6'-tetramethyl-3,3'-bis(tert-butyl)-1,1'-biphenyl-2,2'-diyl)isopropyl phosphite
((S)-5,5',6,6'-tetramethyl-3,3'-bis(tert-butyl)-1,1'-biphenyl-2,2'-diyl)-(rac)-1-phenylethyl phosphite
((R)-5,5',6,6'-tetramethyl-3,3'-bis(tert-butyl)-1,1'-biphenyl-2,2'-diyl)-(rac)-1-phenylethyl phosphite
((S)-5,5',6,6'-tetramethyl-3,3'-bis(tert-butyl)-1,1'-biphenyl-2,2'-diyl)-(S)-1-phenylethyl phosphite
((R)-5,5',6,6'-tetramethyl-3,3'-bis(tert-butyl)-1,1'-biphenyl-2,2'-diyl)-(S)-1-phenylethyl phosphite
((S)-5,5',6,6'-tetramethyl-3,3'-bis(tert-butyl)-1,1'-biphenyl-2,2'-diyl)-(R)-1-phenylethyl phosphite
((R)-5,5',6,6'-tetramethyl-3,3'-bis(tert-butyl)-1,1'-biphenyl-2,2'-diyl)-(R)-1-phenylethyl phosphite
((S)-5,5',6,6'-tetramethyl-3,3'-bis(tert-butyl)-1,1'-biphenyl-2,2'-diyl)diphenylmethyl phosphite
((R)-5,5',6,6'-tetramethyl-3,3'-bis(tert-butyl)-1,1'-biphenyl-2,2'-diyl)diphenylmethyl phosphite
((S)-5,5',6,6'-tetramethyl-3,3'-bis(tert-butyl)-1,1'-biphenyl-2,2'-diyl)methyl phosphite
((R)-5,5',6,6'-tetramethyl-3,3'-bis(tert-butyl)-1,1'-biphenyl-2,2'-diyl)methyl phosphite
((S)-5,5',6,6'-tetramethyl-3,3'-bis(tert-butyl)-1,1'-biphenyl-2,2'-diyl)-2,6-dimethylphenyl phosphite
((R)-5,5',6,6'-tetramethyl-3,3'-bis(tert-butyl)-1,1'-biphenyl-2,2'-diyl)-2,6-dimethylphenyl phosphite
((S)-5,5',6,6'-tetramethyl-3,3'-bis(tert-butyl)-1,1'-biphenyl-2,2'-diyl)-2,6-diiso-propylphenyl phosphite
((R)-5,5',6,6'-tetramethyl-3,3'-bis(tert-butyl)-1,1'-biphenyl-2,2'-diyl)-2,6-diiso-propylphenyl phosphite
((S)-5,5',6,6'-tetramethyl-3,3'-bis(tert-butyl)-1,1'-biphenyl-2,2'-diyl)phenyl phosphite
((R)-5,5',6,6'-tetramethyl-3,3'-bis(tert-butyl)-1,1'-biphenyl-2,2'-diyl)phenyl phosphite
((S)-5,5',6,6'-tetramethyl-3,3'-bis(tert-butyl)-1,1'-biphenyl-2,2'-diyl)ethyl phosphite
((R)-5,5',6,6'-tetramethyl-3,3'-bis(tert-butyl)-1,1'-biphenyl-2,2'-diyl)ethyl phosphite
((S)-5,5',6,6'-tetramethyl-3,3'-bis(tert-butyl)-1,1'-biphenyl-2,2'-diyl)-4-tert-butylphenyl phosphite
((R)-5,5',6,6'-tetramethyl-3,3'-bis(tert-butyl)-1,1'-biphenyl-2,2'-diyl)-4-tert-butylphenyl phosphite
((S)-1,1'-binaphthyl-2,2'-diyl)isopropyl phosphite
((R)-1,1'-binaphthyl-2,2'-diyl)isopropyl phosphite
((S)-1,1'-binaphthyl-2,2'-diyl)neopentyl phosphite
((R)-1,1'-binaphthyl-2,2'-diyl)neopentyl phosphite
((S)-1,1'-binaphthyl-2,2'-diyl)phenyl phosphite
((R)-1,1'-binaphthyl-2,2'-diyl)phenyl phosphite
((S)-11,1'-binaphthyl-2,2'-diyl)benzyl phosphite and
((R)-1,1'-binaphthyl-2,2'-diyl)benzyl phosphite, even greater preference being given to the last eight compounds named.

Steps a) and c) are optionally carried out in the presence of a base.

Step a) is preferably carried out without base, step c) in the presence of a base.

Useful bases for the reaction of steps a) and c) are in each case independently alkaline earth metal or alkali metal hydrides, hydroxides, amides, alkoxides, carbonates or hydrogen carbonates, for example sodium hydride, sodium amide, lithium diethylamide, sodium methoxide, sodium ethoxide, potassium tert-butoxide, sodium hydroxide, potassium hydroxide, sodium carbonate, potassium carbonate, potassium hydrogen carbonate or sodium hydrogen carbonate, organolithium compounds such as n-butyllithium, aromatic nitrogen bases such as pyridines, for example pyridine, 2,6-lutidine, 2-, 3-, 4-picoline, and also preferably tertiary amines, for example trimethylamine, triethylamine, tributylamine, di-isopropylethylamine, tetramethylguanidine, N,N-dimethylaniline, piperidine, N-methylpiperidine, N,N-dimethylaminopyridine, diazabicyclooctane (DABCO), diazabicyclononene (DBN) or diazabicycloundecene (DBU).

Particular preference is given to using triethylamine as the base.

When aromatic nitrogen bases or tertiary amines are used for steps a) and c), any precipitated hydrohalides of the bases used are preferably removed before their further reaction or workup. The removal is preferably effected by filtration.

Steps a) and c) are optionally carried out in the presence of a solvent. Step a) is preferably carried out without solvent, step c) preferably in the presence of a solvent.

Useful solvents are in particular organic solvents such as aliphatic or aromatic, optionally halogenated hydrocarbons, for example petroleum ether, benzene, toluene, the isomeric xylenes, chlorobenzene, the isomeric dichlorobenzenes, hexane, cyclohexane, dichloromethane or chloroform, and also ethers such as diethyl ether, diisopropyl ether, dioxane, tetrahydrofuran, methyl tert-butyl ether or ethylene glycol dimethyl or ethylene glycol diethyl ether. Preferred organic solvents are toluene, diethyl ether, tetrahydrofuran and methyl-tert-butyl ether.

In step a), when base is used, the molar ratio of base to compounds of the formula (II) is, for example and with preference, 0.7:1 to 2.0:1, particularly preferably 0.9:1 to 1.2:1 and very particularly preferably 1.0:1 to 1.1:1.

In step c), the molar ratio of base to compounds of the formula (IV) is, for example and with preference, 1.4:1 to 4.0:1, particularly preferably 1.8:1 to 2.5:1 and very particularly preferably 2.0:1 to 2.2:1.

In step a), the reaction temperature is, for example and with preference, −20 to 100° C., particularly preferably −15 to 40° C. and very particularly preferably −10 to 25° C.

The same temperature range is applied to step c).

In step a), the molar ratio of compounds of the formula (II) to compounds of the formula (III) is, for example, 1.2:1 to 10:1, preferably 1.5:1 to 4:1 and particularly preferably 1.5:1 to 2.5:1. Larger amounts of compounds of the formula (III) are possible, but uneconomic.

In step c), the molar ratio of compounds of the formula (IV) to compounds of the formula (V) is, for example, 0.5:1 to 5:1, preferably 0.8:1 to 1.5:1 and particularly preferably 0.8:1 to 1.0:1.

In step b), a distillative purification takes place.

The distillation may be carried out, for example and with preference, at a pressure of 0.001 to 1000 hPa, preferably from 0.001 to 100 hPa and particularly preferably 0.001 to 50 hPa.

Both the compounds of the formula (I) obtained after workup and the reaction solutions of compounds of the formula (I) obtained after any filtration can be used directly for the synthesis of transition metal complexes containing compounds of the formula (I).

The workup can be effected, for example and with preference, in such a way that, optionally after removing any precipitates, the solvent is initially removed distillatively and the compounds of the formula (I) are purified further by recrystallization or reprecipitation.

A distinct advantage of the compounds of the formula (I) prepared according to the invention is that they are obtained in very high purity and are in particular virtually free of troublesome by-products, in particular phosphates. Nevertheless, phosphites frequently occur in the form of a highly viscous form tending to foam formation, which complicates the handling.

The invention therefore further includes a process for preparing transition metal complexes containing compounds of the formula (I) which comprises both the steps a), b) and c) according to the invention and further step d), the reaction of the compounds of the formula (I) obtained in steps a) to c) with transition metal compounds.

Useful solvents for the reaction of compounds of the formula (I) with transition metal compounds are in particular the same organic solvents that are suitable for the reaction of step c). Preference is given to methylene chloride.

In one preferred embodiment, the compounds of the formula (I) can be used directly in step d) in the form of their solutions, as obtained in step c), optionally after removal of precipitates.

Alternatively, the solutions as obtained in step c), optionally after removing precipitates, can be concentrated, taken up again in solvents and subsequently used in step d).

Transition metal complexes containing compounds of the formula (I) are preferably transition metal complexes of ruthenium, rhodium, iridium, nickel, palladium and platinum, preferably those of ruthenium, rhodium and iridium.

Particularly preferred transition metal complexes containing compounds of the formula (I) are those of the formula (Xa)

$$[(I)_4 M^1]An^1 \qquad (Xa)$$

where (I) is in each case independently, preferably identically, a compound of the formula (I) and $M^1$ is rhodium or iridium and $An^1$ is methanesulphonate, trifluoromethanesulphonate, tetrafluoroborate, hexafluorophosphate, perchlorate, hexafluoroantimonate, tetra(bis-3,5-trifluoromethylphenyl)borate or tetraphenylborate or those of the formula (Xb)

$$[(I)_2 L_2 M^1]An^1 \qquad (Xb)$$

where (I) is in each case independently, preferably identically, a compound of the formula (I) and $M^1$ is rhodium or iridium and $An^1$ is methanesulphonate, trifluoromethanesulphonate, tetrafluoroborate, hexafluorophosphate, perchlorate, hexafluoroantimonate, tetra(bis-3,5-trifluoromethylphenyl)borate or tetraphenylborate and L is in each case a $C_2$–$C_{12}$ alkene, for example ethylene or cyclooctene or a nitrile, for example acetonitrile, benzonitrile or benzyl nitrile, $L_2$ together is a ($C_4$–$C_{12}$)-diene, for example norbornadiene or 1,5-cyclooctadiene, and those of the formula (XI)

$$[(I)_4 Hal_2 M^1{}_2] \qquad (XI)$$

where (I) is in each case independently, preferably identically, a compound of the formula (I) and $M^1$ is rhodium or iridium and Hal is chlorine, bromine or iodine, preferably chlorine, or those of the formula (XII)

$$[(I)_2(arene)Hal_2 Ru] \qquad (XII),$$

where
(I) is in each case independently, preferably identically, a compound of the formula (I) and arene is a coordinated aromatic compound having 6 to 12 ring carbon atoms which may also be substituted by up to 6 radicals which are each independently selected from the group of $C_1$–$C_8$-alkyl, benzyl and phenyl, and arene is preferably benzene or naphthalene, each of which may be substituted by up to 6 radicals which are each independently selected from the group of methyl, ethyl, n-propyl, isopropyl and tert-butyl, and is particularly preferably mesitylene, cumene or benzene, and Hal is chlorine, bromine or iodine, preferably chlorine, or those of the formula (XIII)

$$[(I)_2(XIV)Hal_2Ru] \quad (XIII)$$

where
(I) is in each case independently, preferably identically, a compound of the formula (I) and Hal is chlorine, bromine or iodine, preferably chlorine, (XIV) represents compounds of the formula (XIV)

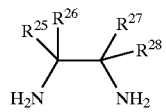

(XIV)

where
$R^{25}$, $R^{26}$, $R^{27}$ and $R^{28}$ are each independently hydrogen, $C_1$–$C_{12}$-alkyl, $C_4$–$C_{14}$-aryl or $C_5$–$C_{15}$-arylalkyl, or in each case two radicals together are a straight-chain or branched $C_3$–$C_{12}$-alkylene radical.

Preferred compounds of the formula (XIV) are:

(S)— and (R)-1,2-diphenylethylene-1,2-diamine, (S)— and (R)-1,2-di-tert-butylethylene-1,2-diamine, (S)— and (R)-1,1-di-(p-methoxyphenyl)-2-isopropylethylene-1,2-diamine, (S)— and (R,R)-16-aminotetracyclo(6.6.2.02,7.09,14]hexadeca-2,4,6,9,11,13-hexaen-15-ylamine and (S)— and (R)-1,2-diaminocyclohexane.

The compounds of the formula (XIV) preferably have a stereoisomeric purity of 90% or more, particularly preferably of 95% or more and very particularly preferably of 98.5% or more.

The invention likewise encompasses the compounds of the formulae (Xa), (Xb), (XI), (XII) and (XIII).

Transition metal complexes containing compounds of the formula (I) are obtained by reacting compounds of the formula (I) with transition metal compounds.

Suitable transition metal compounds are preferably those of the formula (XV)

$$M^2(An^2)_p \quad (XV)$$

where
$M^2$ is ruthenium, rhodium, iridium, nickel, palladium or platinum and $An^2$ is chloride, bromide, acetate, nitrate, methanesulphonate, trifluoromethanesulphonate or acetylacetonate and p is ruthenium, rhodium and iridium is 3, for nickel, palladium and platinum is 2, or transition metal compounds of the formula (XVI)

$$M^2(An^2)_p L^1_2 \quad (XVI)$$

where
$M^2$ is ruthenium, rhodium, iridium, nickel, palladium or platinum and $An^2$ is chloride, bromide, acetate, methanesulphonate, trifluoromethanesulphonate, tetrafluoroborate, hexafluorophosphate, perchlorate, hexafluoroantimonate, tetra(bis-3,5-trifluoromethylphenyl)borate or tetraphenylborate and p is rhodium and iridium is 1, for nickel, palladium, platinum and ruthenium is 2 and $L^1$ is in each case $C_2$–$C_{12}$-alkene, for example ethylene or cyclooctene, or a nitrile, for example acetonitrile, benzonitrile or benzylnitrile, or $L^1_2$ together is a ($C_4$–$C_{12}$)-diene, for example norbornadiene or 1,5-cyclooctadiene, or transition metal compounds of the formula (XVII)

$$[M^2L^2An^2_2]_2 \quad (XVII)$$

where
M is ruthenium and $L^2$ is an aryl radical, for example cymene, mesityl, phenyl or cyclooctadiene, norbornadiene or methylallyl and $An^2$ is chloride, bromide, acetate, methanesulphonate, trifluoromethanesulphonate, tetrafluoroborate, hexafluorophosphate, perchlorate, hexafluoroantimonate, tetra(bis-3,5-trifluoromethylphenyl)borate or tetraphenylborate or transition metal compounds of the formula (XVIII)

$$M^3_p[M^2(An^3)_4] \quad (XVIII)$$

where
$M^2$ is palladium, nickel, iridium or rhodium and $An^3$ is chloride or bromide and $M^3$ is lithium, sodium, potassium, ammonium or organic ammonium and p is rhodium and iridium is 3, for nickel, palladium and platinum is 2, or transition metal compounds of the formula (XIX)

$$[M^2(L^3)_2]An^4 \quad (XIX)$$

where
$M^2$ is iridium or rhodium and $L^3$ is a ($C_4$–$C_{12}$)-diene, for example norbornadiene or 1,5-cyclooctadiene $An^4$ is a noncoordinating or weakly coordinating anion, for example methanesulphonate, trifluoromethanesulphonate, tetrafluoroborate, hexafluorophosphate, perchlorate, hexafluoroantimonate, tetra(bis-3,5-trifluoromethylphenyl)borate or tetraphenylborate.

Additional examples of suitable transition metal compounds include $Ni(1,5$-cyclooctadiene$)_2$, $Pd_2$(dibenzylidenacetone$)_3$, $Pd[PPh_3]_4$, cyclopentadienyl$_2$Ru, $Rh(acac)(CO)_2$, $Ir(pyridine)_2(1,5$-cyclooctadiene), $Cu(phenyl)Br$, $Cu(phenyl)Cl$, $Cu(phenyl)I$, $Cu(PPh_3)_2Br$, $[Cu(CH_3CN)_4]BF_4$ and $[Cu(CH_3CN)_4]PF_6$ or multinuclear bridged complexes, for example $[Rh(1,5$-cyclooctadiene)Cl]_2$ and $[Rh(1,5$-cyclooctadiene)Br]_2$, $[Rh(ethene)_2Cl]_2$, $[Rh(cyclooctene)_2Cl]_2$.

Preferred transition metal compounds are those which are suitable for preparing compounds of the formulae (X) to (XIII).

These are in particular:

$[Rh(COD)Cl]_2$ (COD=1,5-cyclooctadiene), $[Rh(COD)_2Br]$, $[Rh(COD)_2]ClO_4$, $[Rh(COD)_2]BF_4$, $[Rh(COD)_2]PF_6$, $[Rh(COD)_2]OTf$, $[Rh(COD)_2]BAr_4$ (Ar=3,5-bistrifluoromethylphenyl) $[Rh(COD)_2]SbF_6$ $RuCl_2(COD)$, [(cymene)RuCl$_2$]$_2$, [(benzene)RuCl$_2$]$_2$, [(mesityl)RuCl$_2$]$_2$, [(cymene)RuBr$_2$]$_2$, [(cymene)RuI$_2$]$_2$, [(cymene)Ru(BF$_4$)$_2$]$_2$, [(cymene)Ru(PF$_6$)$_2$]$_2$, [(cymene)Ru(BAr$_4$)$_2$]$_2$, (Ar=3,5-bistrifluoromethylphenyl), [(cymene)Ru(SbF$_6$)$_2$]$_2$, [Ir(COD)$_2$Cl]$_2$, [Ir(COD)$_2$]PF$_6$, [Ir(COD)$_2$]ClO$_4$, [Ir(COD)$_2$]SbF$_6$, [Ir(COD)$_2$]BF$_4$, [Ir(COD)$_2$]OTf, [Ir(COD)$_2$]BAr$_4$(Ar=3,5-bistrifluoromethyl phenyl),

[Rh(nbd)Cl]$_2$(nbd=norbornadiene), [Rh(nbd)$_2$Br], [Rh(nbd)$_2$]ClO$_4$, [Rh(nbd)$_2$]BF$_4$, [Rh(nbd)$_2$]PF$_6$, [Rh(nbd)$_2$]OTf, [Rh(nbd)$_2$]BAr$_4$ (Ar=3,5-bistrifluoromethylphenyl) [Rh(nbd)$_2$]SbF$_6$RuCl$_2$(nbd), [Ir(nbd)$_2$]PF$_6$, [Ir(nbd)$_2$]ClO$_4$, [Ir(nbd)$_2$]SbF$_6$[Ir(nbd)$_2$]BF$_4$, [Ir(nbd)$_2$]OTf, [Ir(nbd)$_2$]BAr$_4$ (Ar=3,5-bistrifluoromethylphenyl), Ir(pyridine)$_2$(nbd), [Ru(DMSO)$_4$Cl$_2$], [Ru(CH$_3$CN)$_4$Cl$_2$], [Ru(PhCN)$_4$Cl$_2$] and [Ru(COD)Cl$_2$]$_n$, and, even greater preference is given to
[(cymene)RuCl$_2$]$_2$, Rh(COD)$_2$OTf, Rh(COD)$_2$ PF$_6$, Rh(COD)$_2$SbF$_6$ and Rh(COD)$_2$BF$_4$.

The amount of the transition metal in the transition metal compound used in the conversion to transition metal complexes containing the compounds of the formula (I) may be, for example, 10 to 100 mol %, based on the compound of the formula (I) used, and preference is given to amounts which are 0 to 10 mol % higher than the desired stoichiometry or the stoichiometry in the transition metal complexes of the formula (X) to (XIII).

The transition metal complexes containing the compounds of the formula (I) obtained in step d) may either be isolated in a manner known per se or used directly as catalysts in the form of the reaction solution obtained in step d).

The invention further encompasses processes for preparing stereoisomerically enriched compounds by asymmetric synthesis, which is characterized in that the catalysts used are transition metal complexes containing the compounds of the formula (I) or transition metal complexes of the formulae (Xa), (Xb), (XI), (XII) and (XIII).

The transition metal complexes containing the compounds of the formula (I) and also compounds of the formulae (Xa), (Xb), (XI), XII) and (XIII) are suitable in particular as catalysts, preferably in a process for preparing stereoisomerically enriched, particularly preferably enantiomerically enriched, compounds.

The invention therefore includes a process for preparing stereoisomerically enriched compounds by asymmetric synthesis, which is characterized in that the catalysts used are transition metal complexes containing the compounds of the formula (I) or transition metal complexes of the formulae (Xa), (Xb), (XI), XII) and (XIII).

Preferred processes for preparing chiral compounds are asymmetric 1,4-additions, asymmetric hydroformylations, asymmetric hydrocyanations, asymmetric Heck reactions and asymmetric hydrogenations, and particular preference is given to asymmetric hydrogenations.

Examples of preferred asymmetric hydrogenations are hydrogenations of prochiral C=C bonds, for example prochiral enamines, olefins, enol ethers, C=O bonds, for example prochiral ketones, and C=N bonds, for example prochiral imines. Particularly preferred asymmetric hydrogenations are hydrogenations of prochiral enamines and olefins.

The advantage of the present invention is that phosphites can be prepared in an efficient manner in high yields virtually without troublesome phosphates. The high product purity also allows the direct use for preparing transition metal complexes which may be used as catalysts.

EXAMPLES

Example 1

Preparation of isopropyl dichlorophosphite

A baked-out three-necked flask equipped with a fitted dropping funnel and distillation attachment and Vigreux column is initially charged with phosphorus tri-chloride (30 ml, 0.34 mol) at −10° C. and 2-propanol (17.5 ml, 0.23 mol) is added slowly via the dropping funnel with constant stirring. After the end of the addition, the mixture is stirred for a further 1 h. Subsequently, isopropyl dichlorophosphite is obtained at 25 mbar (b.p.$_{25}$:31° C.). In this way, 14.0 g (52% of theory) are obtained.

Example 2

Preparation of ((R)-1,1'-binaphthyl-2,2'-diyl)isopropyl phosphite

A baked-out 100 ml Schlenk flask is initially charged with 75 ml of dried, degassed tetrahydrofuran and 2.41 g (15.0 mmol) of isopropyl dichlorophosphite under argon atmosphere at room temperature and cooled to 0° C. The mixture is admixed with 4.19 ml (30.1 mmol) of abs. triethylamine and stirred for 5 min. Afterwards, 4.28 g (15.0 mmol) of (R)-1,1'-binaphthyl-2,2'-diol are added as a solid. After stirring for a further 15 min., the ice bath is removed and the mixture stirred at room temperature overnight. The solids are filtered off from the reaction solution under protective gas and the solvent is removed under reduced pressure. 4.4 g (79% of theory) of ((R)-1,1'-binaphthyl-2,2'-diyl)isopropyl phosphite are obtained. $^{31}$P NMR (162 MHz, CD$_2$Cl$_2$): δ=147.1 ppm.

Example 3

Preparation of ((R)-1,1'-binaphthyl-2,2'-diyl)benzyl phosphite

A baked-out 250 ml Schlenk flask is initially charged with 100 ml of dried, degassed tetrahydrofuran and 2.5 ml (13.6 mmol) of benzyl dichlorophosphite under argon atmosphere at room temperature and cooled to 0° C. The mixture is admixed with 3.82 ml (27.4 mmol) of abs. triethylamine and stirred for 5 min. Afterwards, 3.90 g (13.6 mmol) of (R)-1, 1'-binaphthyl-2,2'-diol is added as a solid. After stirring for a further 15 min., the ice bath is removed and the mixture stirred at room temperature overnight. The solids are filtered off from the reaction solution under protective gas and the solvent is removed under reduced pressure. 3.7 g (73% of theory) of ((R)-1,1'-binaphthyl-2,2'-diyl)benzyl phosphite are obtained. $^{31}$P NMR (162 MHz, CD$_2$Cl$_2$): δ=140.7 ppm.

Example 4

Preparation of ((S)-1,1'-binaphthyl-2,2'-diyl)phenyl phosphite

A baked-out 100 ml Schlenk flask is initially charged with 25 ml of dried, degassed tetrahydrofuran and 1.27 g (6.5 mmol) of phenyl dichlorophosphite under argon atmosphere at room temperature and cooled to 0° C. The mixture is admixed with 1.82 g (13.1 mmol) of abs. triethylamine and stirred for 5 min. Afterwards, 1.87 g (6.5 mmol) of (S)-1,1'-binaphthyl-2,2'-diol is added as a solid. After stirring for a further 15 min., the ice bath is removed and the mixture stirred at room temperature overnight. The solids are filtered off from the reaction solution under protective gas and the solvent is removed under reduced pressure. 1.91 g (74% of theory) of ((S)-1,1'-binaphthyl-2,2'-diyl)phenyl phosphite are obtained. $^{31}$P NMR (162 MHz, CD$_2$Cl$_2$): δ=145.8 ppm.

Example 5

Preparation of [{((R)-1,1'-binaphthyl-2,2'-diyl)isopropyl phosphite}$_2$(COD)Rh]OTf In a dry Schlenk flask, 74 mg of Rh(COD)$_2$OTf (0.158 mmol) and 118 mg (0.315 mmol) of ((R)-1,1'-binaphthyl-2,2'-diyl)isopropyl phosphite from Example 2 were weighed in, the vessel was evacuated three times and charged with argon, and the mixture was admixed with 2 ml of CH$_2$Cl$_2$. After heating to 50° C., an orange solution and some brown residue were obtained. A layer of 6 ml of n-hexane was then applied. After a diffusion time of 10 h, transparent, slightly yellowish crystals which had grown on the glass wall could be isolated and were analysed by single crystal x-ray structure analysis. $^{31}$P NMR (162 MHz, CD$_2$Cl$_2$): 138, b; 133, d,$^1$J$_{PRh}$=221 Hz; 129, d, $^1$J$_{PRh}$=234 Hz; 125, b [ppm].

Example 6

Preparation of [{((R)-1,1'-binaphthyl-2,2'-diyl) isopropyl phosphite}$_4$Rh]OTf

In a dry Schlenck flask (or initially separate in two flasks), 136 mg of Rh(COD)$_2$OTf (0.291 mmol) and 435 mg (1.163 mmol) of ((R)-1,1'-binaphthyl-2,2'-diyl)isopropyl phosphite from Example 2 were weighed in, the vessel was evacuated and charged with argon 3 times and the mixture was admixed with 1 ml of argonized THF (or the vessels were argonized, 2 ml of CH$_2$Cl$_2$ were added to each and the metal solution was added to the ligand solution). After mixing, a slightly cloudy solution was obtained. A layer of 15 ml of argonized hexane was then applied. After a diffusion time of 16 h, the resulting brown-yellow precipitate could be filtered off. After drying, 470 mg of product were obtained, corresponds to 93% based on L$_4$RhOTf (1749 g/mol). $^{31}$P NMR (162 MHz, CDCl$_3$): 138, b; 133, d, $^1$J$_{PRh}$=221 Hz; 129, d, $^1$J$_{PRh}$=234 Hz; 125, b [ppm].

Example 7

Preparation of [{((R)-1,1'-binaphthyl-2,2'-diyl)isopropyl phosphite}$_4$Cl$_2$Rh$_2$]

In a dry Schlenck flask, 39 mg of Rh(COD)$_2$Cl$_2$ (0.079 mmol) and 118 mg (0.314 mmol) of ((R)-1,1'-binaphthyl-2,2'-diyl)isopropyl phosphite from Example 2 were weighed in, the vessel was evacuated and charged with argon 3 times and the mixture was admixed with 1 ml of argonized toluene After mixing, a solution was obtained. A layer of 15 ml of argonized hexane was then applied. After diffusion, the resulting yellow precipitate could be filtered off. After drying, 125 mg of product were obtained, corresponding to 89% based on L$_4$Rh$_2$Cl$_2$ (1774 g/mol). The substance is hardly soluble in standard solvents.

Example 8

Preparation of [{((R)-1,1'-binaphthyl-2,2'-diyl)isopropyl phosphite}$_2$-{(S,S)-1,2-diphenylethylene-1,2-diamine}Cl$_2$Ru]

In a round-bottomed flask, 90 mg of RuCl$_2$(p-cymene) (0.147 mmol) and 220 mg (0.588 mmol) of ((R)-1,1'-binaphthyl-2,2'-diyl) isopropyl phosphite from Example 2 were weighed in, and 10 ml of degassed DMF were added under argon. The mixture was stirred at 90° C. for 3 h, and a red solution was obtained. The solution was allowed to warm to RT and 62 mg of (S,S)-DPEN (0.294 mmol) were added. Afterwards, the mixture was stirred for a further 24 h. The DMF was removed under high vacuum and the residue was dissolved in 5 ml of THF or dichloromethane, and the product was precipitated using 15 ml of diethyl ether, filtered off with suction and dried (130 mg, 77%). (Red solid). FD-MS: 1133 (M++1); $^{31}$P NMR (162 MHz, CDCl$_3$): 155, s [ppm].

Example 9

Preparation of [{((R)-1,1'-binaphthyl-2,2'-diyl)neopentyl phosphite}$_2$-{(S,S)-1,2-diphenylethylene-1,2-diamine}Cl$_2$Ru]

In a round-bottomed flask, 90 mg of RuCl$_2$(p-cymene) (0.147 mmol) and 236 mg (0.588 mmol) of ((R)-1,1'-binaphthyl-2,2'-diyl)neopentyl phosphite which was obtained in a similar manner to Example 2 were weighed in, and 10 ml of degassed DMF were added under argon. The mixture was stirred at 90° C. for 3 h, and a red solution was obtained. The solution was allowed to warm to RT and 62 mg of (S,S)-DPEN (0.294 mmol) were added. Afterwards, the mixture was stirred for a further 19 h. The DMF was removed under high vacuum and the residue was dissolved in 5 ml of THF or dichloromethane, and the product was precipitated using 15 ml of diethyl ether, filtered off with suction and dried (red solid). $^1$H NMR (400 MHz, CDCl$_3$): 7.04–8.05, 30H; 6.89, t, 2H; $^3$J$_{HH}$=8 Hz; 6.72, d, 2H; $^3$J$_{HH}$=8Hz; 4.44, d, 2H; $^3$J$_{HH}$=10 Hz; 4.15, d, 2H ; $^3$J$_{HH}$=10 Hz; 3.78, bs, 2H; 3.49, d, 2H; $^3$J$_{HH}$=10 Hz; 2.79, d, 2H; $^3$J$_{HH}$=10 Hz; 0.67, s, 18H [ppm]. $^{31}$P NMR (162 MHz, CDCl$_3$):155, s [ppm].

Example 10

[{((R)1,1'-binaphthyl-2,2'-diyl)isopropyl phosphite}$_2$(COD)Rh]BF$_4$

In a three-necked flask, 19.70 g of Rh(COD)$_2$BF$_4$ (48.5 mmol) were weighed in, and 50 ml of THF and 150 ml of dichloromethane were added under argon. Afterwards, 27.77 g (86% purity by NMR, 86 mmol) of ((R)-1,1'-binaphthyl-2,2'-diyl)isopropyl phosphite from Example 2, dried beforehand under reduced pressure for 24 h, were added dissolved in 40 ml of THF. The reddish solution was stirred for 15 minutes. The product was then rapidly precipitated using 800 ml of n-hexane. In some cases, only a brown oily residue forms at the bottom of the vessel. In this case, the product was taken up again in 200 ml of THF, precipitated with 600 ml of n-hexane and filtered off. Orange/yellow, crystalline solid. Weight: 44.05 g, based on L$_2$Rh(COD)BF$_4$ gives a yield of 93–98%. $^1$H NMR (400 MHz, CDCl$_3$): 8.26, d, 2H, $^3$J$_{HH}$=8 Hz; 8.08, d, 2H, $^3$J$_{HH}$=8 Hz; 8.04, d, 2H, $^3$J$_{HH}$=9 Hz; 7.89, d, 2H, $^3$J$_{HH}$=8 Hz; 7.81, d, 2H,; $^3$J$_{HH}$=9 Hz; 7.58–7.47, m, 6H; 7.39–7.23, m, 8H; 5.8, m, 2H; 4.75, m, 2H; 4.32, m, 2H; 2.22–2.08, m, 4H; 1.94–1.84, m, 2H; 1.50, d, 6H, $^3$J$_{HH}$=6Hz; 1.3, m, 8H [ppm]. $^{31}$P NMR (162 MHz, CDCl$_3$): 120, d, $^1$J$_{PRh}$=258 Hz.

Example 11

Preparation of [{((R)-1,1'-binaphthyl-2,2'-diyl)isopropyl phosphite}$_2$(COD)Rh]SbF$_6$ In a dry Schlenck flask, 18 mg of Rh(COD)$_2$SbF$_6$ (0.033 mol) and 25 mg (0.066 mmol) of ((R)-1,1'-binaphthyl-2,2'-diyl)isopropyl phosphite from Example 2 were weighed in, the vessel was evacuated and charged with argon 3 times and the mixture was admixed with 0.3 ml of argonized CH$_2$Cl$_2$. Afterwards, the mixture was stirred for 2 h and the product was precipitated using 5 ml of diethyl ether, filtered off with suction and dried. $^1$H NMR (400 MHz, CDCl$_3$): 8.27, d, 2H, $^3J_{HH}$=8 Hz; 8.07, d, 2H, $^3J_{HH}$=8 Hz; 8.03, d, 2H, $^3J_{HH}$=9 Hz; 7.96, d, 2H, $^3J_{HH}$=8 Hz; 7.85, d, 2H, ; $^3J_{HH}$=9 Hz; 7.60–7.47, m, 6H; 7.39–7.23, m, 8H; 5.80, m, 2H; 4.77, m, 2H; 4.25, m, 2H; 2.20–2.03, m, 4H; 1.85, m, 2H; 1.53, d, 6H, $^3J_{HH}$=6 Hz; 1.27, m, 8H; [ppm]. $^{31}$P NMR (162 MHz, CDCl$_3$): 119, d, $^1J_{PRh}$=258 Hz.

Example 12

Preparation of [{((R)-1,1'-binaphthyl-2,2'-diyl)isopropyl phosphite}$_4$Rh]PF$_6$ In a dry Schlenck flask, 15 mg of Rh(COD)$_2$PF$_6$ (0.033 mol) and 25 mg (0.066 mmol) of ((R)-1,1'-binaphthyl-2,2'-diyl)isopropyl phosphite from Example 2 were weighed in, the vessel was evacuated and charged with argon 3 times and the mixture was admixed with 0.3 ml of argonized CH$_2$Cl$_2$. Afterwards, the mixture was stirred for 2 h and the product was precipitated using 5 ml of diethyl ether, filtered off with suction and dried. $^1$H NMR (400 MHz, CDCl$_3$): 8.25, d, 2H, $^3J_{HH}$=8 Hz; 8.05, d, 2H, $^3J_{HH}$=8 Hz; 8.02, d, 2H, $^3J_{HH}$=9 Hz; 7.95, d, 2H, $^3J_{HH}$=8 Hz; 7.83, d, 2H,; $^3J_{HH}$=9 Hz; 7.60–7.45, m, 6H; 7.39–7.23, m, 8H; 5.78, m, 2H; 4.75, m, 2H; 4.25, m, 2H; 2.20–2.03, m, 4H; 1.85, m, 2H; 1.50, d, 6H, $^3J_{HH}$=6 Hz; 1.27, m, 8H; [ppm]. $^{31}$P NMR (162 MHz, CDCl$_3$): 119, d, $^1J_{PRh}$=258 Hz.

The invention claimed is:

1. Process for preparing compounds of the formula (I)

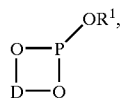
(I)

where
D is an unsubstituted or substituted 1,1'-biphenyl-2,2'-diyl- or 1,1'-binaphthyl-2,2'-diyl radical and
R$^1$ is a radical selected from the group of C$_1$–C$_{12}$-alkyl, C$_2$–C$_{12}$-alkenyl, C$_1$–C$_{12}$-halogenalkyl, C$_5$–C$_{15}$-arylalkyl and C$_4$–C$_{14}$-aryl, with the proviso that
R$^1$ has a molar mass of 215 or less,
comprising
in a step a) reacting
compounds of the formula (II), PHal$_3$ (II)

where Hal is in each case independently chlorine, bromine or iodine,
with compounds of the formula (III),

R$^1$—OH (III)

where
R$^1$ is as defined above
to give compounds of the formula (IV)

R$^1$OPHal$_2$ (IV)

where
R$^1$ and Hal are each as defined above,
in a step b) ditillatively purifying
the compounds of the formula (IV) of a) and
in a step c), reacting
the compounds of the formula (IV), purified in step b) with compounds of the formula (V)

D(OH)$_2$ (V)

where
D is as defined above
to give compounds of the formula (I).

2. Process according to claim 1, characterized in that step c) is carried out in the presence of a base.

3. Process according to claim 1, characterized in that R$^1$ is a radical which is selected from the group of C$_1$–C$_8$-alkyl, C$_5$–C$_{15}$-arylalkyl and C$_4$–C$_{14}$-aryl, with the proviso that
R$^1$ has a molar mass of 200 or less.

4. Process according to claim 1, characterized in that D is an unsubstituted or substituted 1,1'-biphenyl-2,2'-diyl radical of the formula (VI)

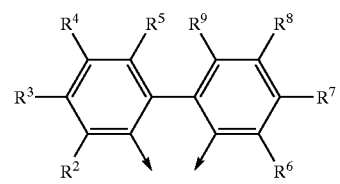
(VI)

or is an unsubstituted or substituted 1,1'-binaphthyl-2,2'-diyl radical of the formula (VII)

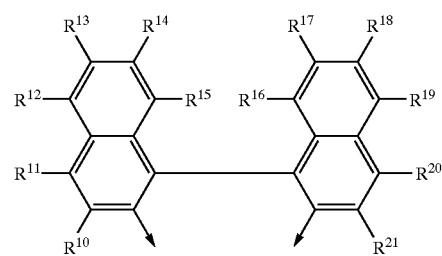
(VII)

where the radicals
R$^2$ to R$^{20}$ are in each case independently selected from the group of hydrogen, fluorine, chlorine, bromine, cyano, protected hydroxyl, C$_1$–C$_{12}$-alkyl, C$_1$–C$_{12}$-halogenalkyl, C$_1$–C$_{12}$-alkoxy, C$_1$–C$_8$-alkylthio, free or protected formyl, C$_4$–C$_{14}$-aryl, tri(C$_1$–C$_8$-alkyl)siloxyl or radicals of the formula (VIII)

A-B-E-F (VIII)

where, each independently,
A is absent or is a C$_1$–C$_8$-alkylene radical and
B is absent or is oxygen, sulphur or NR$^{21}$
where
R$^{21}$ is hydrogen, C$_1$–C$_{12}$-alkyl or C$_4$–C$_{14}$-aryl and
E is a carbonyl group and
F is R$^{22}$, OR$^{22}$, NHR$^{23}$ or NR$^{23}$R$^{24}$ where
R$^{22}$ is C$_1$–C$_{12}$-alkyl or C$_6$–C$_{10}$-aryl and
R$^{23}$ and R$^{24}$ are each independently C$_1$–C$_8$-alkyl or C$_4$–C$_{14}$-aryl, or NR$^{23}$R$^{24}$ together is a cyclic amino radical having 4 to 12 carbon atoms, and in each case two adjacent radicals from R$^2$ to R$^{20}$ together optionally form a nonaromatic ring and in each case two of the radicals from R$^1$ to R$^{20}$ optionally are bridging.

5. Process according to claim 1, characterized in that enantiomerically enriched compounds of the formula (V) are used.

6. Process according to claim 1, characterized in that the compounds of formula (I) are selected from the group consisting of:
((S)-5,5'-dichloro-6,6'-dimethoxy-1,1'-biphenyl-2,2'-diyl) isopropyl phosphite
((R)-5,5'-dichloro-6,6'-dimethoxy-1,1'-biphenyl-2,2'-diyl)isopropyl phosphite
((R)-5,5'-dichloro-6,6'-dimethoxy-1,1'-biphenyl-2,2'-diyl)-(R)-1-phenylethyl phosphite
((R)-5,5'-dichloro-6,6'-dimethoxy-1,1'-biphenyl-2,2'-diyl)-(S)-1-phenylethyl phosphite
((S)-5,5'-dichloro-6,6'-dimethoxy-1,1'-biphenyl-2,2'-diyl)-(R)-1-phenylethyl phosphite
((S)-5,5'-dichloro-6,6'-dimethoxy-1,1'-biphenyl-2,2'-diyl)-(S)-1-phenylethyl phosphite
((S)-5,5'-dichloro-6,6'-dimethoxy-1,1'-biphenyl-2,2'-diyl) cyclohexyl phosphite
((R)-5,5'-dichloro-6,6'-dimethoxy-1,1'-biphenyl-2,2'-diyl)cyclohexyl phosphite
((S)-5,5'-dichloro-6,6'-dimethoxy-1,1'-biphenyl-2,2'-diyl) phenyl phosphite
((R)-5,5'-dichloro-6,6'-dimethoxy-1,1'-biphenyl-2,2'-diyl)phenyl phosphite
((S)-5,5'-dichloro-6,6'-dimethoxy-1,1'-biphenyl-2,2'-diyl)-2,6-dimethylphenyl phosphite
((R)-5,5'-dichloro-6,6'-dimethoxy-1,1'-biphenyl-2,2'-diyl)-2,6-dimethylphenyl phosphite
((S)-5,5',6,6'-tetramethyl-3,3'-bis(tert-butyl)-1,1'-biphenyl-2,2'-diyl)isopropyl phosphite
((R)-5,5',6,6'-tetramethyl-3,3'-bis(tert-butyl)-1,1'-biphenyl-2,2'-diyl)isopropyl phosphite
((S)-5,5',6,6'-tetramethyl-3,3'-bis(tert-butyl)-1,1'-biphenyl-2,2'-diyl)-(rac)-1-phenylethyl phosphite
((R)-5,5',6,6'-tetramethyl-3,3'-bis(tert-butyl)-1,1'-biphenyl-2,2'-diyl)-(rac)-1-phenylethyl phosphite
((S)-5,5',6,6'-tetramethyl-3,3'-bis(tert-butyl)-1,1'-biphenyl-2,2'-diyl)-(S)-1-phenylethyl phosphite
((R)-5,5',6,6'-tetramethyl-3,3'-bis(tert-butyl)-1,1'-biphenyl-2,2'-diyl)-(S)-1-phenylethyl phosphite
((S)-5,5',6,6'-tetramethyl-3,3'-bis(tert-butyl)-1,1'-biphenyl-2,2'-diyl)-(R)-1-phenylethyl phosphite
((R)-5,5',6,6'-tetramethyl-3,3'-bis(tert-butyl)-1,1'-biphenyl-2,2'-diyl)-(R)-1-phenylethyl phosphite
((S)-5,5',6,6'-tetramethyl-3,3'-bis(tert-butyl)-1,1'-biphenyl-2,2'-diyl)-diphenylmethyl phosphite
((R)-5,5',6,6'-tetramethyl-3,3'-bis(tert-butyl)-1,1'-biphenyl-2,2'-diyl)-diphenylmethyl phosphite
((S)-5,5',6,6'-tetramethyl-3,3'-bis(tert-butyl)-1,1'-biphenyl-2,2'-diyl)methyl phosphite
((R)-5,5',6,6'-tetramethyl-3,3'-bis(tert-butyl)-1,1'-biphenyl-2,2'-diyl)methyl phosphite
((S)-5,5',6,6'-tetramethyl-3,3'-bis(tert-butyl)-1,1'-biphenyl-2,2'-diyl)-2,6-dimethylphenyl phosphite
((R)-5,5',6,6'-tetramethyl-3,3'-bis(tert-butyl)-1,1'-biphenyl-2,2'-diyl)-2,6-dimethylphenyl phosphite
((S)-5,5',6,6'-tetramethyl-3,3'-bis(tert-butyl)-1,1'-biphenyl-2,2'-diyl)-2,6-diiso-propylphenyl phosphite
((R)-5,5',6,6'-tetramethyl-3,3'-bis(tert-butyl)-1,1'-biphenyl-2,2'-diyl)-2,6-diiso-propylphenyl phosphite
((S)-5,5',6,6'-tetramethyl-3,3'-bis(tert-butyl)-1,1'-biphenyl-2,2'-diyl)phenyl phosphite
((R)-5,5',6,6'-tetramethyl-3,3'-bis(tert-butyl)-1,1'-biphenyl-2,2'-diyl)phenyl phosphite
((S)-5,5',6,6'-tetramethyl-3,3'-bis(tert-butyl)-1,1'-biphenyl-2,2'-diyl)ethyl phosphite
((R)-5,5',6,6'-tetramethyl-3,3'-bis(tert-butyl)-1,1'-biphenyl-2,2'-diyl)ethyl phosphite
((S)-5,5',6,6'-tetramethyl-3,3'-bis(tert-butyl)-1,1'-biphenyl-2,2'-diyl)-4-tert-butylphenyl phosphite
((R)-5,5',6,6'-tetramethyl-3,3'-bis(tert-butyl)-1,1'-biphenyl-2,2'-diyl)-4-tert-butylphenyl phosphite
((S)-1,1'-binaphthyl-2,2'-diyl)isopropyl phosphite
((R)-1,1'-binaphthyl-2,2'-diyl)isopropyl phosphite
((S)-1,1'-binaphthyl-2,2'-diyl)neopentyl phosphite
((R)-1,1'-binaphthyl-2,2'-diyl)neopentyl phosphite
((S)-1,1'-binaphthyl-2,2'-diyl)phenyl phosphite
((R)-1,1'-binaphthyl-2,2'-diyl)phenyl phosphite
((S)-1,1,'-binaphthyl-2,2'-diyl)benzyl phosphite and
((R)-1,1'-binaphthyl-2,2'-diyl)benzyl phosphite.

7. Process according to claim 1, characterized in that the distillation in step b) is carried out a pressure from 0.001 to 1000 hPa.

8. Process according to claim 1 further comprising as step d), reacting the compounds of the formula (I) obtained in steps a) to c) with transition metal compounds.

9. Process according to claim 8, characterized in that solutions of compounds of the formula (I), as obtained in step c), are used directly in step d), optionally after removing precipitates.

10. Process according to claim 8, characterized in that solutions of compounds of the formula (I), as obtained in step c), are concentrated, optionally after removing precipitates, the compounds of the formula (I) are taken up again in solvents and subsequently provided for reaction in step d).

11. Process according to claim 8, characterized in that transition metal compounds containing compounds of the formula (I) are those of the formula (Xa), $$[(I)_4 M^1]An^1 \qquad (Xa)$$

where
(I) is in each case independently, a compound of the formula (I) and
M$^1$ is rhodium or iridium and
An$^1$ is methanesulphonate, trifluoromethanesulphonate, tetrafluoroborate, hexafluorophosphate, perchlorate, hexafluoroantimonate, tetra(bis 3,5-trifluoromethylphenyl)borate or tetraphenylborate or
those of the formula (Xb)

$$[(I)_2 L_2 M^1]An^1 \qquad (Xb)$$

where
(I) is in each case independently a compound of the formula (I) and
M$^1$ is rhodium or iridium and
An$^1$ is methanesulphonate, trifluoromethanesulphonate, tetrafluoroborate, hexafluorophosphate, perchlorate, hexafluoroantimonate, tetra(bis 3,5-trifluoromethylphenyl)borate or tetraphenylborate and
L is in each case a C$_2$–C$_{12}$-alkene, or
L$_2$ together is a (C$_4$–C$_{12}$)-diene and
those of the formula (XI)

$$[(I)_4 Hal_2 M^1{}_2] \qquad (XI)$$

where
(I) is in each case independently a compound of the formula (I) and
$M^1$ is rhodium or iridium and
Hal is chlorine, bromine or iodine or
those of the formula (XII)

  (XII), where
(I) is in each case independently a compound of the formula (I) and
arene is a coordinated aromatic compound having 6 to 12 ring carbon atoms which is optionally substituted by up to 6 radicals which are each independently selected from the group of $C_1$–$C_8$-alkyl, benzyl and phenyl and
Hal is chlorine, bromine or iodine, or
those of the formula (XIII)

  (XIII)

where
(I) is in each case independently a compound of the formula (I) and
Hal is chlorine, bromine or iodine,
(XIV) represents compounds of the formula (XIV)

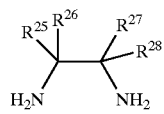  (XIV)

where
$R^{25}$, $R^{26}$, $R^{27}$ and $R^{28}$ are each independently hydrogen, $C_1$–$C_{12}$-alkyl, $C_4$–$C_{14}$-aryl or $C_5$–$C_{15}$-arylalkyl radicals, or in each case two radicals together are a straight-chain or branched $C_3$–$C_{12}$-alkylene radical.

12. A transition metal complex having the formula (Xa)

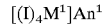  (Xa), where
(I) is in each case independently a compound of the formula (I) as defined in claim 1 and
$M^1$ is rhodium or iridium and
$An^1$ is methanesulphonate, trifluoromethanesulphonate, tetrafluoroborate, hexafluorophosphate, perchlorate, hexafluoroantimonate, tetra(bis 3,5-trifluoromethylphenyl)borate or tetraphenylborate.

13. A transition metal complex having the formula (Xb)

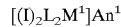  (Xb)

where
(I) is in each case independently a compound of the formula (I) as defined in claim 1 and
$M^1$ is rhodium or iridium and
$An^1$ is methanesulphonate, trifluoromethanesulphonate, tetrafluoroborate, hexafluorophosphate, perchlorate, hexafluoroantimonate, tetra(bis 3,5-trifluoromethylphenyl)borate or tetraphenylborate and
L is in each case a $C_2$–$C_{12}$-alkene, or a nitrile, or
$L_2$ together is a ($C_4$–$C_{12}$)-diene.

14. A transition metal complex having the formula (XI)

  (XI), where
(I) is in each case independently, a compound of the formula (I) as defined in claim 1 and
$M^1$ is rhodium or iridium and
Hal is chlorine, bromine or iodine.

15. A transition metal complex having the formula (XII)

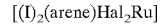  (XII), where
(I) is in each case independently a compound of the formula (I) as defined in claim 1 and
arene is a coordinated aromatic compound having 6 to 12 ring carbon atoms which is optionally substituted by up to 6 radicals which are each independently selected from the group of $C_1$–$C_8$-alkyl, benzyl and phenyl.
Hal is chlorine, bromine or iodine.

16. A transition metal complex having the formula (XIII)

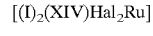  (XIII), where
(I) is in each case independently, a compound of the formula (I) and
Hal is chlorine, bromine or iodine,
(XIV) represents compounds of the formula (XIV)

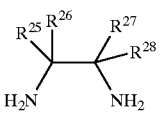  (XIV)

where
$R^{25}$, $R^{26}$, $R^{27}$ and $R^{28}$ are each independently hydrogen, $C_1$–$C_{12}$-alkyl, $C_4$–$C_{14}$-aryl or $C_5$–$C_{15}$-arylalkyl, or in each case two radicals together are a straight-chain or branched $C_3$–$C_{12}$-alkylene radical.

* * * * *